(12) United States Patent
Pettigrew et al.

(10) Patent No.: US 10,191,054 B2
(45) Date of Patent: Jan. 29, 2019

(54) MICROFLUIDIC DEVICE FOR FULL BLOOD COUNT

(75) Inventors: David M. Pettigrew, Eindhoven (GB); James D. Gwyer, Eindhoven (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 618 days.

(21) Appl. No.: 13/146,324

(22) PCT Filed: Jan. 26, 2010

(86) PCT No.: PCT/IB2010/050327
§ 371 (c)(1),
(2), (4) Date: Jul. 27, 2011

(87) PCT Pub. No.: WO2010/086786
PCT Pub. Date: Aug. 5, 2010

(65) Prior Publication Data
US 2011/0275111 A1   Nov. 10, 2011

(30) Foreign Application Priority Data

Jan. 27, 2009   (EP) .................................... 09151420

(51) Int. Cl.
*G01N 33/569*   (2006.01)
*B01L 3/00*   (2006.01)
(Continued)

(52) U.S. Cl.
CPC .. *G01N 33/56972* (2013.01); *B01L 3/502776* (2013.01); *G01N 15/12* (2013.01); *G01N 15/1484* (2013.01); *G01N 33/721* (2013.01); *G01N 33/80* (2013.01); *B01L 2200/10* (2013.01); *B01L 2300/0627* (2013.01); *B01L 2300/087* (2013.01); *B01L 2300/0816* (2013.01); *B01L 2300/0864* (2013.01); *G01N 2015/008* (2013.01); *G01N 2015/0069* (2013.01); *G01N 2015/0084* (2013.01);
(Continued)

(58) Field of Classification Search
None
See application file for complete search history.

(56) References Cited

U.S. PATENT DOCUMENTS

| | | | |
|---|---|---|---|
| 4,275,031 A | 6/1981 | Fischer et al. | |
| 4,654,197 A | 3/1987 | Lilja et al. | |
| 4,853,338 A * | 8/1989 | Benezra et al. | 436/66 |
| 5,064,282 A | 11/1991 | Curtis | |
| 5,155,044 A * | 10/1992 | Ledis et al. | 436/17 |
| 5,763,280 A | 6/1998 | Li | |

(Continued)

FOREIGN PATENT DOCUMENTS

CN   1975380 A   6/2007

OTHER PUBLICATIONS

Bassett (2001) Proc Inst Mech Eng 215:861-881.*
(Continued)

*Primary Examiner* — Melanie Yu Brown
*Assistant Examiner* — Richard Moerschell

(57) ABSTRACT

A device for full blood count includes first channel and second channels separated from each other. The device further includes a first inlet configured to provide a whole blood sample to the first and second channels, a second inlet configured to provide a lysis agent for white blood cell count in to the first channel, a third inlet configured to provide a quench solution to the first channel, and a fourth inlet configured to provide a lysis agent for hemoglobin measurement to the second channel.

13 Claims, 12 Drawing Sheets

(51) Int. Cl.
  *G01N 15/12* (2006.01)
  *G01N 15/14* (2006.01)
  *G01N 33/72* (2006.01)
  *G01N 33/80* (2006.01)
  *G01N 15/00* (2006.01)
  *G01N 15/10* (2006.01)

(52) U.S. Cl.
  CPC ............ *G01N 2015/1037* (2013.01); *G01N 2015/1062* (2013.01); *Y10T 137/0402* (2015.04)

(56) References Cited

U.S. PATENT DOCUMENTS

| | | | | |
|---|---|---|---|---|
| 6,830,729 | B1* | 12/2004 | Holl | G01N 15/14 356/246 |
| 2002/0098589 | A1* | 7/2002 | Crews | G01N 15/1456 436/10 |
| 2002/0149766 | A1 | 10/2002 | Bardell | |
| 2003/0040115 | A1 | 2/2003 | Li | |
| 2003/0073089 | A1 | 4/2003 | Mauze | |
| 2003/0104631 | A1 | 6/2003 | Carver | |
| 2004/0094418 | A1* | 5/2004 | Cox | B01F 5/0068 204/450 |
| 2005/0153459 | A1* | 7/2005 | Kopf-Sill | B01L 3/5027 436/183 |
| 2005/0255600 | A1* | 11/2005 | Padmanabhan et al. | 436/63 |
| 2006/0263889 | A1 | 11/2006 | Lang | |
| 2007/0009386 | A1 | 1/2007 | Padmanabhan | |
| 2007/0031289 | A1 | 2/2007 | Cox et al. | |
| 2010/0151443 | A1* | 6/2010 | Xiang | B82Y 15/00 435/5 |

OTHER PUBLICATIONS

Pugia, Michael J. et al "Microfluidic Tool Box as Technology Platform for Hand-Held Diagnostics" Clinical Chemistry, vol. 51, No. 10, 2005, pp. 1923-1932.

Floriano, Pierre N. et al "Microchip-Based Enumeration of Human White Blood Cells" Methods in Molecular Biology, vol. 385; 2005, pp. 53-64.

Oshiro, I. et al "New Method for Hemoglobin Determination by Using SOdium Lauryl Sulfate (SLS)" Clinical Biochemistry, vol. 15, No. 2, Apr. 1982, pp. 83-88.

Cheung, K.S. et al "Impedance Spectroscopy Flow Cytometry: On-Chip Label-Free Cell Differentiation" Cytometry A, 2005, vol. 65(2); pp. 124-132.

Van Kampen et al:"Standardization of Hemoglobinometry II. The Hemiglobincyanide Method"; Clinica Chimica Acta, vol. 6, 1961, pp. 538-544.

Beckman Coulter:"ACV Differential Technology and Case Studies—Hematology"; Company Bulletin 9151, 2000, 26 Page Document.

Drabkin et al: "Spectrophotometric Studiesii. Preparations From Washed Blood Cells; Nitric Oxide Hemoglobin and Sulfhemoglobin"; University of Pennsylvania, Jun. 1935, pp. 51-65.

Ekberg et al: "A Real Point-Of-Care System for Complete Blood Counting"; Point of Care, vol. 4, No. 1, Mar. 2005.

Hughs:"Market Trends in Point-Of-Care Testing"; Point of Care, Vol. 1, No. 2, 2002, pp. 84-94.

Johnson et al: "Analysis of Emergency Department Test Ordering Patterns in an Urban Academic Medical Center: Can the Point-Of-Care Option in a Satellite Laboratory Provide Suffiencient Menu to Permit Full Service Testing"; Point-Of-Care, vol. 6, No. 2, Jun. 2007, pp. 134-138.

Munoz et al: "Utility of Point-Of-Care Haemoglobin Measurement in the Hemocue-B Haemoglobin for the Initial Diagnosis of Anaemia"; Clin. Lab Haem. 2005, vol. 27, pp. 99-104.

Vanzetti: "An Azide-Methemoglobin Method for Hemoglobin Determination in Blood"; J. Lab Clin Med, 1966, vol. 67 (1), pp. 116-126.

Sethu et al: "Continuous Flow Microfluidic Device for Rapid Erythrocyte Lysis"; Anal. Chem. 2004, vol. 76, pp. 6247-6253.

Takubo et al: "Evaluation of Palmtop-Sized Blood Cell Counteri Prototype Palm LC"; Point-Of-Care, vol. 6, No. 3, Sep. 2007, pp. 174-177.

Von Schenck et al : "Evaluation of "Henocue," A New Device for Determining Hemoglobin"; Clin. Chem. 32/3, 1986, pp. 526-529.

\* cited by examiner

MICROFLUIDIC DEVICE FOR FULL BLOOD COUNT

FIELD OF THE INVENTION

The present invention relates to microfluidic methods and devices. More particularly, the present invention relates to a microfluidic device for full blood count (FBC), a method for forming such a micro fluidic device and a method for performing a full blood count test (FBC test) using such a microfluidic device.

BACKGROUND OF THE INVENTION

Full blood count (FBC) is a diagnostic test that is used to measure cellular composition of blood. It may give information about the status of an immune system of a patient, about the ability of the blood to disseminate oxygen and/or about the ability of the blood to effectively clot. As such, it is a fundamental test that is often used as an initial "general purpose" diagnostic tool or as a more targeted monitoring solution. Examples of care cycles that include a full blood count as a monitoring tool include oncology, arthritis and Crohn's disease. As many as 300 million FBC tests are performed each year in the developed world.

FBC diagnostic parameters and their clinical indicators are summarized in Table 1 and Table 2 hereunder. These parameters are generated from several individual measurements, specifically a white blood cell (WBC) differential count, a red blood cell (RBC) count, a platelet count and a hemoglobin (Hb) measurement (see also FIG. 1).

TABLE 1

FBC Clinical Parameters relating to the red blood cells.

| Diagnostic parameter | Details | Clinical Significance | |
| --- | --- | --- | --- |
| | | Decrease | Increase |
| Hemoglobin (Hb) | Concentration of Hb in lysed whole blood (g/dl) | Hemolytic anaemia<br>Haemorrhage<br>Poor diet<br>Bnone marrow failure<br>Renal disease<br>Normal pregnancy<br>Rheumatoid/collagen vascular disease<br>Multiple myeloma<br>Leukaemia<br>Hodgkin disease | Erythrocytosis:<br>Congenital heart disease<br>Chronic hypoxia (shortage of oxygen in the body).<br>Severe dehydration<br>Excess RBC production by bone marrow |
| RBC count | Number of RBCs per $mm^3$ | Haemorrhage<br>Poor diet<br>Bone marrow failure<br>Renal Disease | Erythrocytosis:<br>Reduced $O_2$ capacity of Haemoglobin<br>Excess RBC production by bone marrow<br>High altitude<br>Severe dehydration<br>Congenital heart disease |
| Mean Corpuscular Volume (MCV) | Average RBC volume | Iron deficiency anaemia<br>Thalassemia | Vitamin B12 deficiency<br>Folic acid deficiency<br>Chemotherapy<br>Liver disease |
| RBC distribution width (RDW) | % variation from mean RBC volume | N/A | Vitamin B12 deficiency<br>Folic acid deficiency<br>Iron deficiency anaemia |
| Mean corpuscular Hemoglobin (MCH) | Average conc. of Hb in each RBC | Microcytic anemia (small RBC and/or less Hb) | Macrocytic anemic (large RBC and/or more Hb) |
| Mean corpuscular Hemoglobin Concentration (MCHC) | Average weight of Hb per RBC | Iron deficiency anemia<br>Thalassemia | Intravascular hemolysis (free Hb in blood) |
| Hematocrit | % (v/v) concentration of RBC's in whole blood | Hb disorder<br>Cirrhosis<br>Hemolytic anaemia<br>Haemorrhage<br>Dietary deficiency<br>Bone marrow failure<br>Renal disease<br>Normal pregnancy<br>Rheumatoid/collagen vascular disease<br>Multiple myeloma<br>Leukemia<br>Hodgkin disease | Polycythemia vera (excess RBC production by bone marrow<br>High altitude<br>Severe dehydration<br>Congenital heart disease |

TABLE 2

FBC Clinical Parameters relating to the white blood cells.

| Diagnostic parameter | Clinical Significance | |
|---|---|---|
| | Decrease | Increase |
| Total white blood cell (WBC) count | Bone marrow suppression due to chemotherapy, radiation Therapy, leukaemia or disease-modifying drugs. | Viral, bacterial, fungal, or parasitic infection. Cancer. Response to certain medications |
| Peripheral Blood Mononuclear Cells (PBMCs) | | |
| Lymphocyte count (cells/mm$^3$) | Sepsis Leukaemia Immunodeficiency Latter stages of an HIV infection Drug therapy (e.g. adrenocorticosteroids) Radiation therapy | Intracellular infection (viral or bacterial) |
| Monocyte count (cells/mm$^3$) | Drug therapy: Prednisone | Viral infections Parasitic infection Chronic inflammatory disorders Tuberculosis (TB) |
| Granulocytes | | |
| Neutrophil count (cells/mm$^3$) | Overwhelming bacterial infection (esp. in elderly) Viral infection Dietary deficiency Aplastic anaemia Radiation therapy Drug therapy: Myelotoxic drugs (as in chemotherapy) | Acute bacterial infection Inflammatory disorders (e.g. rheumatoid arthritis) Myelecystic lukemia Metabolic disorders Trauma Physical or emotional stress |
| Eosinophil count (cells/mm$^3$) | Increased adrenosteroid production | Allergic reaction. Autoimmune disease. Parasitic infections. Leukaemia |
| Basophil count (cells/mm$^3$) | Myeloproliferative disease Lukemia | Acute allergic reaction Hyperthyroidism Stress |

Currently, large scale commercial laboratory instruments known as hematology analyzers are used to automatically perform all measurements that comprise the FBC. The high cost and complexity of these devices, coupled to the need for venous blood, means that they are mostly large scale, centralized facilities.

There is a clear clinical need for performing FBC in a near patient setting, particularly for applications that require a full blood count to monitor the progression and/or treatment of a disease. Microfluidic point of care devices have been developed which are capable of measuring individual components of the FBC. In that area, Hb measuring devices, WBC counters capable of performing a white blood cell differential and platelet count devices, devices which optically count and determine size of red blood cells are available.

For cell counting, current hematology analyzers typically employ electrical coulter counting and/or optical scattering methods to count and differentiate white cells and to count and determine size of the red blood cells and platelets.

At the moment only few examples of microfluidic coulter counter technologies exist. One example combines a coulter counter with a Hb measurement. Another example of counting cells is by flow-through impedance spectroscopy. This is a new flow cytometry analysis which is especially suited for a micro fluidic format. This technique is capable of differentiating between lymphocytes, monocytes and neutrophils in lysed blood, and of counting and sizing red blood cells and platelets.

The current "gold-standard" for Hb measurement is the photometric cyanmethaemoglobin (HbCN) method [see van, K. E. and W. G. Zijlstra, Standardization of hemoglobinometry II, The hemiglobincyanide method, Clin Chim Acta, 1961, 6, p. 38-44]. This method involves chemical lysis of the red blood cells and subsequent labelling of all the Hb that these cells release with a cyanide ion. The labels produce a defined absorption profile with a maximum at 540 nm. By measuring the optical absorption at 540 nm, the concentration of Hb can be determined. Furthermore, the high stability of HbCN means that it is easy to supply a calibration standard.

The most common red blood cell lysis/cyanide conversion reagent is known as Drabkin's reagent. Drabkin's reagent contains Potassium Cyanide, which is extremely toxic. This reagent only works for very large dilutions in whole blood (1:251), since red blood cell lysis relies on the low ionic strength of the reagent to induce osmotic shock. This large dilution causes an inherent imprecision in the method. Furthermore, to measure the optical absorption at 540 nm, very long optical path lengths of ~1 cm are required. Finally, in some pathological samples, turbidity can lead to erroneously high absorption readings, which in turn will give rise to an incorrect Hb concentration.

To avoid the problems associated with toxicity and turbidity, many other optical means of measuring Hb have been developed. Examples of these will be described below.

A known point of care device uses sodium azide to convert the Hb to an azide-coordinated Hb derivative (azidemethemoglobin, HbN3). This method itself lends to short path length (0.1 mm) absorption spectroscopy, since dry reagents remove the need for dilution of the whole blood. Two absorbance readings are taken to determine the HbN3 concentration, i.e. one at the absorption maximum (565 nm) and one at 800 nm to correct for turbidity.

For the point of care WBC/Hb counter, a RBC lysis solution has been developed that preserves the WBCs while at the same time labeling the Hb molecule with imidazole. In a similar way as described above, the optical absorption of the imidazole labeled Hb species is measured at two wavelengths, i.e. one at the absorption peak and one to correct for turbidity and scattering effects for the white blood cells. The same solution may also be passed through a coulter counter to perform the cell count.

Another known lysis/Hb conversion reagent is based on sodium lauryl sulphate/sodium dodecyl sulphate (SLS/SDS). The SDS lyses all the blood cells and labels the Hb to get an SDS-coordinated derivative. Since SDS is a surfactant molecule, turbidity correction is not necessary and so a single absorption reading at 535 nm is taken to determine the Hb concentration. This method is designed for high dilutions of Hb, so the inherent imprecision present in the HbCN measurement is still present in the HbSDS one.

All the above described devices and techniques are capable of performing specific measurements from a fingerprick of blood. However, none of the above described devices and techniques are capable of measuring all parameters that are required for an FBC at ones. In other words, none of the devices and techniques described above are able to perform a complete FBC test at the point of care.

SUMMARY OF THE INVENTION

It is an object of embodiments of the present invention to provide a microfluidic device for full blood count (FBC), a method for forming such a microfluidic device and a method for performing a full blood count test using such a microfluidic device.

The above objective is accomplished by a method and device according to the present invention.

The microfluidic device for full blood count comprises:
a first measurement channel,
a second measurement channel separated from the first measurement channel,
a first inlet for providing a whole blood sample to the first and second measurement channel,
a second inlet for providing a lysis agent for white blood cell count in to the first channel,
a third inlet for providing a quench solution to the first channel, and
a fourth inlet for providing a lysis agent for hemoglobin measurement to the second channel.

The separation of the first and second measurement channel allows different chemistries to be used and also allows the detection of particles (in particular the detection of cells with different properties) by different detection means, such as impedance measurement means and/or optical detection means.

The microfluidic device may furthermore comprise means for determining white blood cell differential count at the end of the first channel.

Preferably the means for determining white blood cell differential count is an impedance measurement means.

The microfluidic device may comprise means for determining properties of red blood cells at the end of the second channel.

Preferably, the means for determining properties of red blood cells comprises an optical measurement means. Red blood cell count, platelets count and Hb can be accurately detected.

The microfluidic device may furthermore comprise a micro fluidic chamber in between the second measurement channel and the optical measurement means.

The microfluidic device may comprise a micro fluidic diluter to enable large dilutions to be performed. In standard laboratory procedure large dilutions are performed in a serial fashion where dilution is achieved by performing several smaller dilutions (such that for a 1:10,000 dilution four sequential 1:10 dilutions of the sample might be performed). Such a procedure requires a skilled individual to perform the many pipetting steps, often using large amounts of reagent and time. In moving such a dilution protocol to a micro fluidic format, for example for use in a medical device to be used by an unskilled individual, it is desirable to reduce the amount of reagent used (lowering the cost of the overall device) and to minimise the time needed to run the device (fast start-up). In addition, as with the lysis device described above, it would be preferable in terms of cost if such a device used as few hydrodynamic pumps as possible. Such a device would have application in a point of care haematology analyser where the quantity of red blood cells within the blood makes large dilution necessary.

It is desirable, for the microfluidic device for cost reasons, that lysis be achieved not only microfluidically but also using as few hydrodynamic pumps as possible. Thus, in an advantageous embodiment of FIG. 7, the microfluidic device has been designed to use only a single hydrodynamic pump 200 sucking on the waste outlet of the microfluidic device. The three solutions involved in the reaction (blood, lysis and quench reagents) are stored under atmospheric pressure in reservoirs within the microfluidic device. The flow rates of the reagents (in μl/min) from these reservoirs as they progress towards the detection chip 33 are dictated by:

A micro fluidic device and methods according to embodiments of the invention are capable of measuring all parameters that are required for an FBC device at the point of care from a finger-prick of blood, i.e. it is capable of measuring WBC differential count, platelet count, RBC count and Hb.

The invention further relates to a method for manufacturing a micro fluidic device for full blood count, the method according to the invention comprises:
providing a first measurement channel,
providing a second measurement channel, the second measurement channel separated from the first measurement channel,
providing a first inlet for providing a whole blood sample to the first and second measurement channel,
providing a second inlet at the first measurement channel for providing a lysis agent for white blood cell count in to the first channel,
providing a third inlet at the first measurement channel for providing a quench solution to the first channel, and
providing a fourth inlet at the second measurement channel for providing a lysis agent for hemoglobin measurement to the second channel.

The invention further relates to a method for performing full blood count, the method comprises:
providing a blood sample to a first and a second measurement channel of a microfluidic device, the first and second measurement channel being separated from each other,
providing a lysis agent suitable for white blood cells to the blood sample in the first channel, providing a quench solution to the blood sample in the first channel, providing a lysis agent for hemoglobin to the blood sample in the second channel, at the end of the first channel performing measurements for determining white blood cell counts, and at the end of the second channel performing measurements for determining properties of red blood cells.

Preferably, the measurements for determining white blood cell counts is performed by impedance measurements.

Preferably, the measurements for determining properties of red blood cells is performed by optical measurements.

In an advantageous embodiment of the method, providing a lysis agent suitable for white blood cells to the blood sample in the first channel is performed by providing a mixture of formic acid and saponin.

In an advantageous embodiment of the method, providing a quench solution to the blood sample in the first channel is performed by providing a solution of sodium chloride and sodium bicarbonate.

In advantageous embodiment of the method, providing a lysis agent for hemoglobin to the blood sample in the second channel is performed by providing a solution of SLS in phosphate buffered saline.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
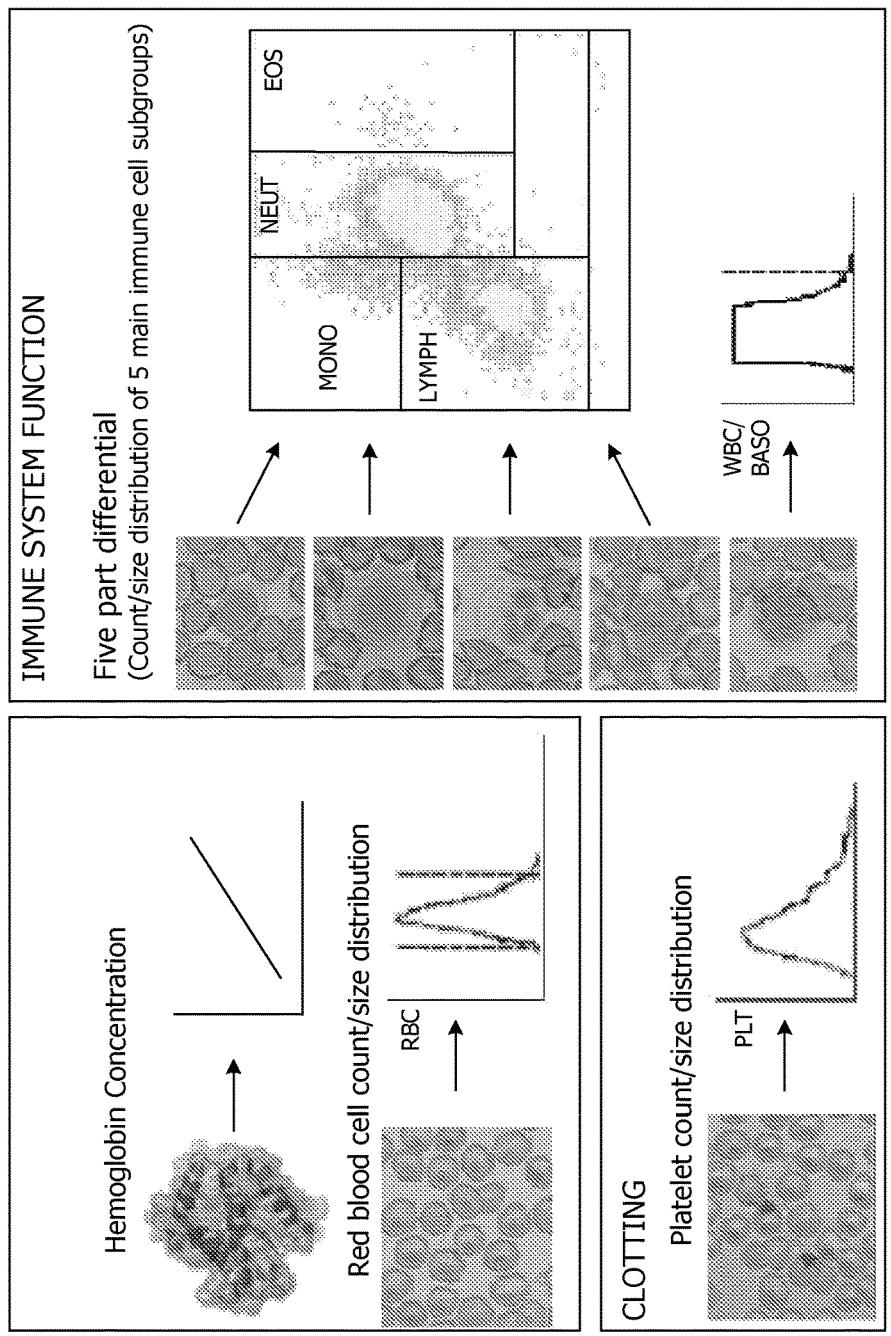
FIG. 1 illustrates different measurements required for a full blood count.

In the different figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The present invention provides a microfluidic device for full blood count (FBC), a method for forming such a microfluidic device and a method for performing a full blood count test (FBC test) using such a microfluidic device.

Several factors prohibit the FBC test from being performed in a point of care setting. First, the cost of purchasing and servicing the hematology analyzer instrument is prohibitive. Skilled technicians are also required to conduct quality control assays to ensure the test gives a result with an acceptable degree of accuracy and precision. Large (4 ml) venous blood samples are required for the test and central lab containment and disinfection facilities are required for handling these potentially infectious samples. Hematology analyzers are very bulky and often contain complex precision optics, meaning that they have a very limited portability. One known type of analyzer, i.e. the Chempaq analyser, is capable of measuring a WBC (white blood cell) differential count, platelet count and hemoglobin (Hb), but is, however, not capable of measuring the RBC (red blood cell) indices.

A microfluidic device and methods according to embodiments of the invention are capable of measuring all parameters that are required for an FBC device at the point of care from a finger-prick of blood, i.e. it is capable of measuring WBC differential count, platelet count, RBC count and Hb.

A key obstacle to a point of care device has been that no one has been able to achieve a microfluidic-based integrated Hb, RBC count, platelet count and white blood cell differential device that is able to process blood from a finger prick, i.e.,EW from a volume of about 10μl to 50μl. The primary reason for this is that it is difficult to combine sample preparation steps required for WBC differentiation and for labeling and detecting Hb in a microfluidic format. The reasons for this are:

The need for dry reagents in case of azide measurement of Hb is not compatible with a "wet" microfluidic system that is required for the calibration and measurement with a microfluidic impedance/coulter counter.

The need for large dilutions/long optical path lengths in current sodium dodecyl sulphate (SDS) and/or cyanmethemoglobin (HbCN) conversion measurements mean that they are not compatible with a simple micro fluidic system. The requirement for very shallow channels; e.g. channels with a diameter of about 50 μm, means that very inaccurate Hb concentrations will be obtained if attempts are made to measure the absorbance of one of these strongly diluted solutions in a microfluidic channel.

For chemical solutions aimed at treating the whole blood to measure a WBC count and Hb from a same sample, there is a danger of erroneous Hb measurements being obtained due to optical scattering by the WBCs.

Many Hb labeling solutions, including those which seek to label with azide or imidazole, are incapable of labeling certain species of Hb, including sulfhemoglobin and carboxyhemoglobin. This leads to errors in the Hb reading for patient samples with high levels of these Hb species.

Problems with turbidity also lead to falsely high Hb readings.

A microfluidic device and method according to embodiments of the invention solve all of the above described problems (see further).

In a first aspect, the present invention provides a microfluidic device for full blood count. The microfluidic device 10 comprises:
  a first measurement channel 11,
  a second measurement channel 12 different and separated from the first measurement channel 11,
  a first inlet 13 for providing a whole blood sample to the first and second measurement channel,
  a second inlet 14 for providing a lysis agent for white blood cell count to the first channel,
  a third inlet 15 for providing a quench solution to the first channel, and
  a fourth inlet 16 for providing a lysis agent for hemoglobin measurement to the second channel.

The microfluidic device according to embodiments of the invention comprises a combination of two microfluidic sample preparation protocols. The first protocol carries out a carefully controlled red blood cell lysis designed to preserve the white blood cells, before delivering the sample to an impedance measurement means (see further), e.g. impedance spectroscope, for a WBC differential measurement. The second protocol lyses the red blood cells and labels the Hb using a SLS (sodium lauryl sulphate) method that requires low dilution factors and therefore short path length absorption spectroscopy (see further).

The use of two separate measurement channels has as an advantage that it allows each lysis solution to be specifically tailored to either a WBC differential count or a Hb measurement. This separation means that problems previously associated with integrated Hb measurement in a micro fluidic format, specifically WBC scattering, turbidity and the conflicting requirements of short path lengths/high dilution, are eliminated.

Figure 2:
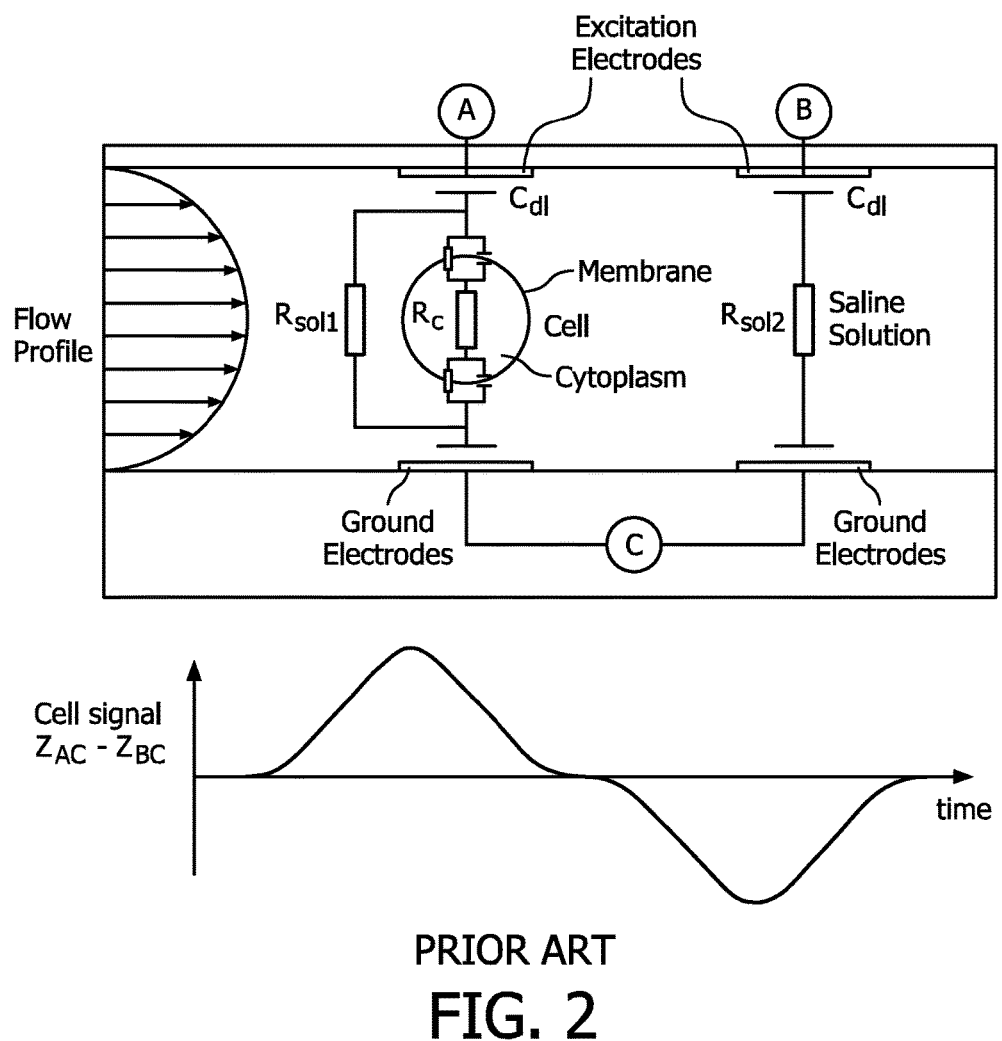
FIG. 2 Flow through impedance spectroscopy.

FIG. 2 shows the impedance measurement means as described in "*Impedance spectroscopy flow cytometry: on-chip label-free cell differentiation*", Cheung, K., S. Gawad, and P. Renaud, Cytometry A, 2005. 65(2): p. 124-132. FIG. 2 shows a side view of the microfluidic channel and a sample cell passing between the measurement and reference electrodes. The Cell Signal is the output of a Lock-In Amplifier measuring the current difference between both electrode pairs. In this way impedance spectroscopy can be performed for different cells.

Figure 3:
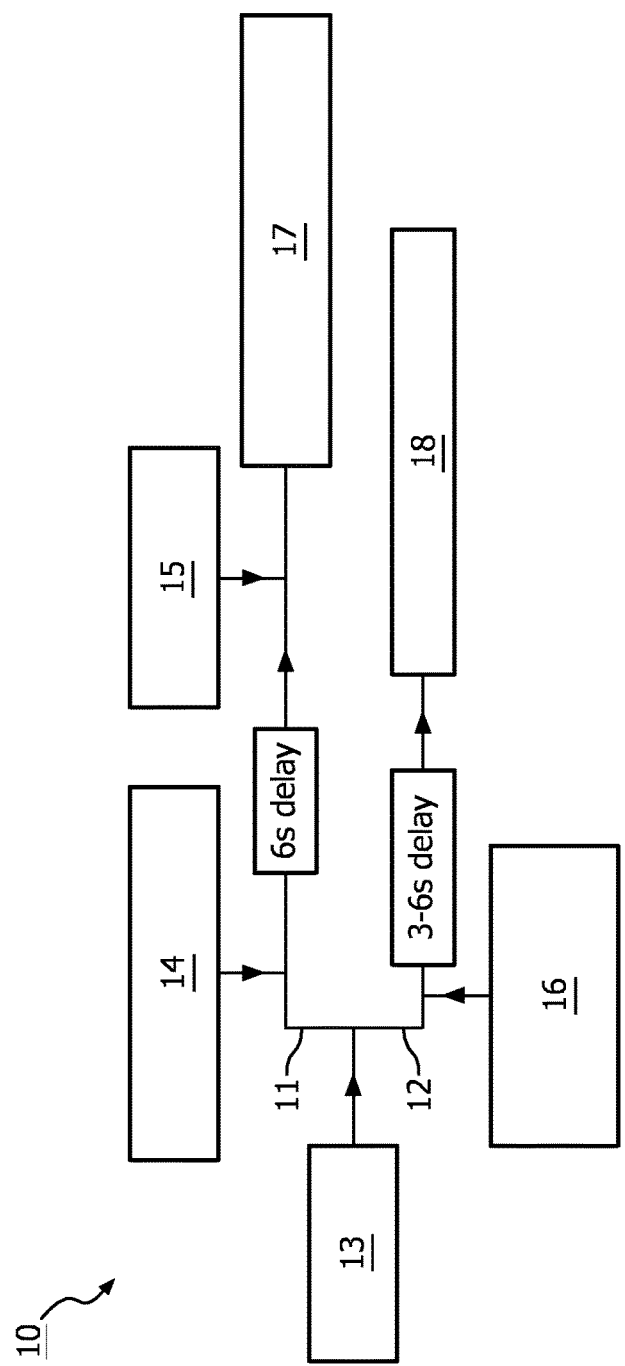
FIG. 3 schematically illustrates a microfluidic device 10 according to an embodiment of the invention.

FIG. 3 schematically illustrates a microfluidic device 10 according to an embodiment of the invention. The microfluidic device 10 comprise a first microfluidic channel 11 and a second microfluidic channel 12. The second micro fluidic channel 12 is different and separated from the first microfluidic channel 11. The microfluidic device 10 comprises a first inlet 13 for providing a whole blood sample to the first and second measurement channels 11, 12. The blood sample may be taken from a patient by a finger prick, because only a limited amount of blood, i.e. a volume of about 10 μm to 50 μl, is required for performing the FBC test with a microfluidic device according to embodiments of the present invention. A second and third inlet 14, 15 are provided at the first channel 11. The second inlet 14 is for providing a lysis agent for WBC differential count to the first channel 11 while the third inlet 15 is for providing a quench solution to the first channel 11. At the end of the first channel 11, means for determining WBC differential count, e.g. an impedance measurement means 17 may be provided while at the end of the second channel 12 means for determining properties of red blood cells, i.e. RBC count, HB and platelet count, e.g. an optical measurement means 18 may be provided.

In a second aspect the present invention also provides a method for performing full blood count. The method comprises:
  providing a blood sample to a first and a second measurement channel 11, 12 of a microfluidic device 10, the first and second measurement channel 11, 12 being separated from each other,
  providing a lysis agent suitable for white blood cells to the blood sample in the first channel 11,
  providing a quench solution to the blood sample in the first channel 11, providing a lysis agent for hemoglobin to the blood sample in the second channel 12,
  at the end of the first channel 11 performing measurements for determining white blood cell count, and
  at the end of the second channel 12 performing measurements for determining properties of red blood cells, i.e. for determining RBC count, platelets count and Hb.

Figure 4A:
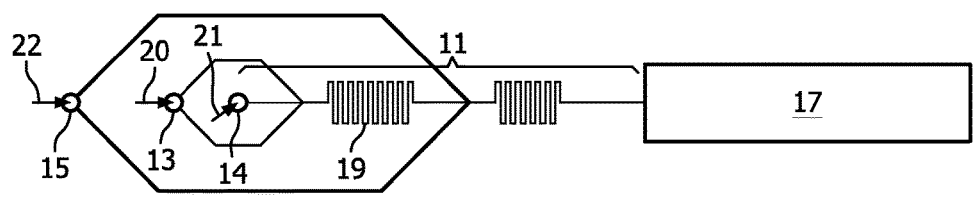
FIG. 4A and 4B illustrate an implementation of a first measurement channel in a microfluidic device according to an embodiment of the present invention and sheath flow interfaces in the microfluidic device both for lysis and for quench.
Figure 4B:
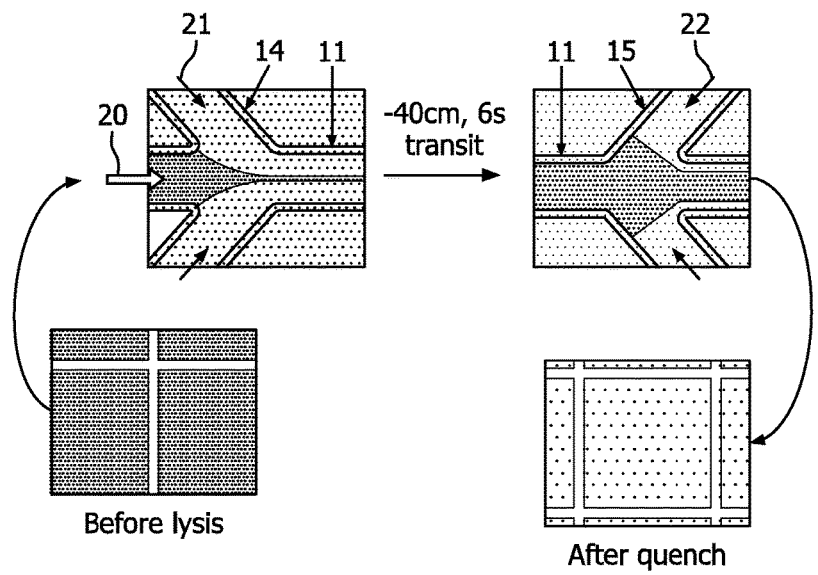

FIG. 4 schematically illustrates what happens in the first measurement channel 11. A whole blood sample is delivered to the first channel 11 through the first inlet 13 (indicated by reference number 20 in FIG. 4). The whole blood sample may be taken from a patient by a finger prick, because only a limited amount of blood, i.e. a volume of about 10 μm to 50 μl, is required for performing the FBC test with a microfluidic device according to embodiments of the present invention. Providing the whole blood sample to the first channel 11 may be done at a known flow rate, e.g. 3 μl/min. A lysis agent, e.g. a mixture of formic acid and saponin, may then be provided to the blood sample in the first measurement channel 11 through a second inlet 14 (indicated by reference number 21 in FIG. 4). This may be performed at a defined flow rate of e.g. 37 μl/min. The lysis agent mixes by diffusion with the whole blood sample over the length of a microfluidic "snake" stage 19 and lyses all the red blood cells which are present in the whole blood sample. The length and channel dimensions of the snake stage 19 are chosen so that the time of contact between the lysis agent and the blood is between 5 and 7 seconds, for example 6 seconds. At the end of the snake stage 19, the quench solution, e.g. a solution comprising sodium chloride and sodium bicarbonate, is provided to the blood sample in the first channel 11 at a defined flow rate of e.g. 16.3 µl/min (indicated by reference number 22 in FIG. 4). The blood sample is then transferred to the measurement means 17 to measure the WBC differential. According to embodiments of the invention, the measurement means 17 to measure the WBC differential may be an impedance measurement means.

Figure 5A:
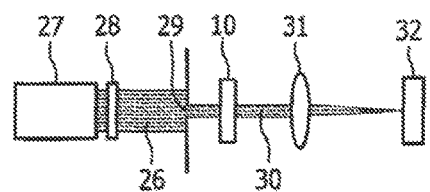
FIGS. 5A and 5B illustrate the concept of hemoglobin measurement in a microfluidic device according to an embodiment of the present invention.
Figure 5B:
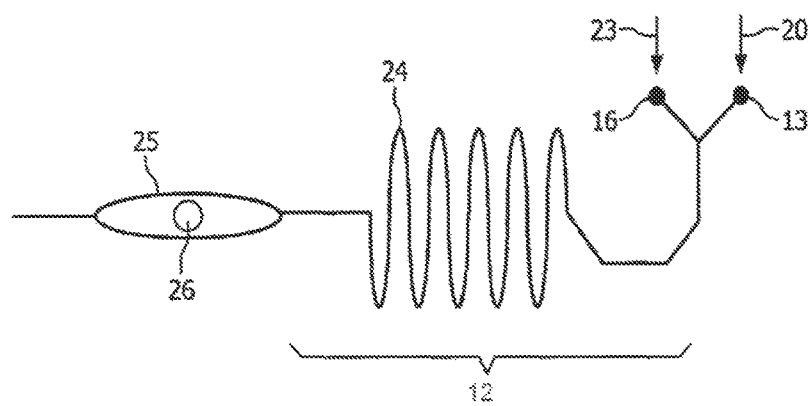

FIG. 5 schematically illustrates what happens in the second measurement channel 12. A whole blood sample is delivered to the second measurement channel 12 through the first inlet 13 (indicated by reference number 20 in FIG. 5B). As providing the whole blood sample to the second measurement channel 12 is also performed through the first inlet 13, according to embodiments of the invention, the blood sample may simultaneously be provided to the first and second measurement channel 11, 12. Providing the blood sample to the second measurement channel 12 may be done at a flow rate, e.g. 1 µl/min.

The flow rate in different microfluidic channels can be different. When designing a system that slows the flow in one channel relative to the other(s) it is common to introduce some form of hydrodynamic resistance. This is achieved either by altering the length of the tube (longer tube, more resistance, slower flow) or by reducing one of the other dimensions of the channel (the method of channel fabrication generally dictates that it is the channel width that is adjusted).

A lysis agent for Hb measurement is provided to the blood sample in the second measurement channel 12 through a fourth inlet 16, e.g. a solution of 150 mM SLS in phosphate buffered saline (PBS), also referred to as SLS reagent (indicated by reference number 23 in FIG. 5B). This may be performed at a constant flow rate of e.g. 4 µl/min. The lysis agent mixes by diffusion with the whole blood sample over the length of a microfluidic "snake" stage 24 and lyses all the red blood cells, platelets and white blood cells. The use of PBS is necessary to prevent the precipitation of the Hb in the second measurement channel 12. The primary lysis agent used in the present example is SLS, which also labels the Hb. At the end of the second measurement channel 12, properties of the red blood cells, i.e. RBC count, platelets count and Hb, are determined by means of measurement means 18. According to embodiments of the invention, measurement means 18 may be an optical measurement means 18. In the case of an optical measurement means 18, according to embodiments of the invention, at the end of the microfluidic "snake" stage 24 the second measurement channel 12 may open into a microfluidic chamber 25. A possible implementation of an optical measurement means 18 that can be used with embodiments of the present invention is illustrated in FIG. 5A. Collimated light 26 at a wavelength of 535 nm may from a light source 27, e.g. a pulsed LED source, be directed at right angles to the microfluidic chamber 25, where it passes through the lysed blood sample. The collimated light 26 is therefore first sent through a filter 28. By means of an aperture 29 it may then be directed towards the microfluidic chamber 25 of the microfluidic device 10. Light 30 transmitted through the device 10 is sent through a lens 31 and is then measured using an amplified photodiode 32.

The depth of the microfluidic chamber 25 may be between 50 µm and 200 µm, and consequently the optical path length of the light going through the micro fluidic chamber 25 may also be between 50 µm and 200 µm. Larger depths for the micro fluidic chamber 25 may be used if the dilution factor required is higher.

Because the WBC measurement and the RBC measurements are separated from each other, a reliable FBC test can be performed which at the end gives a result for all parameters of the FBC test in once.

With the microfluidic device 10 and method according to embodiments of the invention, turbidity correction is not required as the high concentration of SLS will dissociate any cell fragments that would otherwise cause the light to scatter. Similarly, since all the WBCs are destroyed, no scattering losses occur due to the presence of white cells.

Figure 6A:
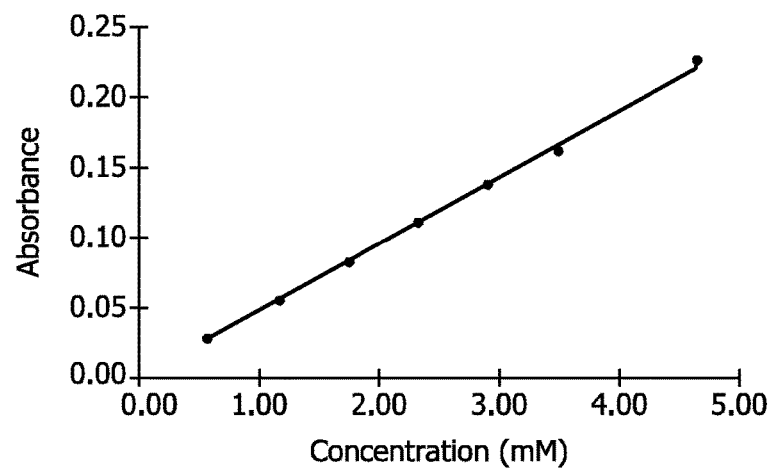
FIGS. 6A and 6B show results of optical measurements of hemoglobin detection according to embodiments of the invention.
Figure 6B:
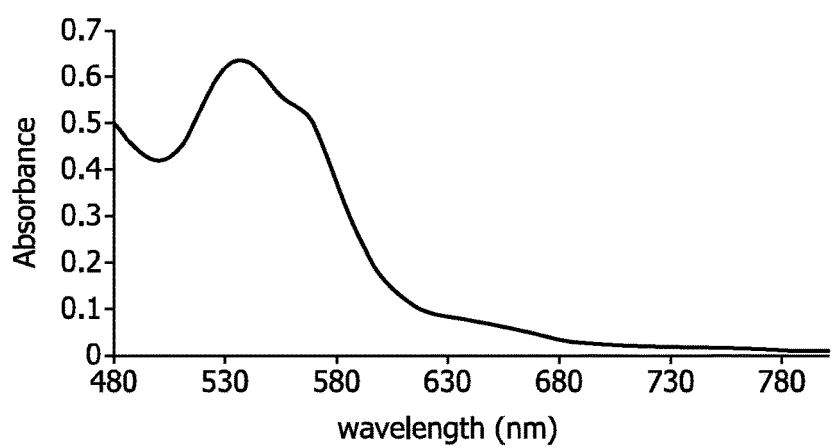

FIG. 6 shows typical data obtained from an integrated Hb measurement as discussed above. FIG. 6A shows that microfluidic sample preparation and optical measurement show good linear behavior on a Beer-Lambert plot over a clinically relevant range. These data are from a whole blood sample. FIG. 6B shows an UV/VIS spectrum of the lysate from the micro fluidic device which confirms that all Hb has successfully been converted into a SLS-coordinated species, with an absorption peak at 535 nm. The zero baseline at 800 nm proves that there is no contribution from scattering by WBCs.

It is desirable, for the microfluidic device for cost reasons, that lysis be achieved not only microfluidically but also using as few hydrodynamic pumps as possible. Thus, in an advantageous embodiment of FIG. 7, the microfluidic device has been designed to use only a single hydrodynamic pump 200 sucking on the waste outlet of the microfluidic device. The three solutions involved in the reaction (blood, lysis and quench reagents) are stored under atmospheric pressure in reservoirs within the microfluidic device. The flow rates of the reagents (in µl/min) from these reservoirs as they progress towards the detection chip are dictated by:

The optimum flow rate of cells for detection at the chip and

Figure 7:
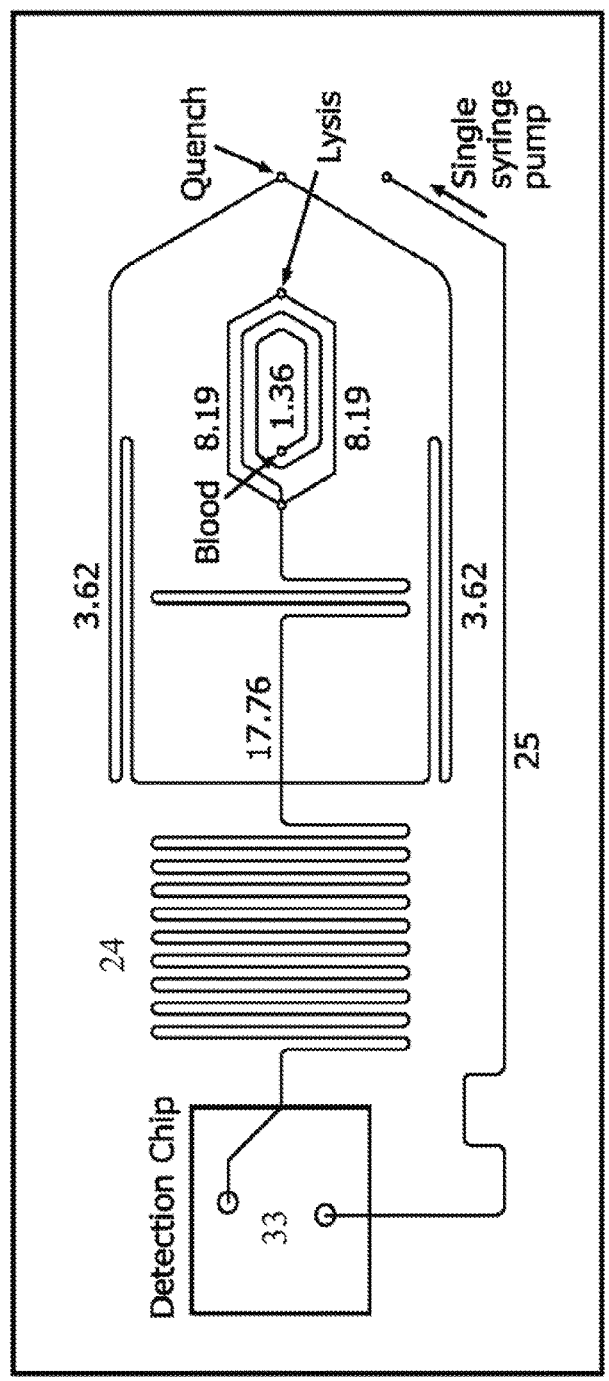
FIG. 7 shows an exemplary embodiment of flow rates through the microfluidic device 10.

The ratios in which the different reagents should be mixed (see FIG. 7).

Where reagents must be in contact with each other for a defined time, this is incorporated into the design through combination of flow rate and channel dimension, thus in the design shown in FIG. 7 a six second contact time following addition of the lysis solution to the blood (flow=17.76 µl/min) is obtained through use of a 8.8 cm section of 200×100 µm channel.

Where reagents are mixed (for example where the lysis reagent is introduced to the blood, or the quench reagent introduced to the lysate) the correct mixing ratios are achieved by adjusting the flow rates of the reagents in the incoming fluidic channels. This adjustment was made by tuning the fluidic resistance of the channels, through variation of the channel height, width or length according to appropriate microfluidic formulae. In FIG. 7 an example of the flow rates through the micro fluidic device is indicated, where the desired flow rate for detection through the detection chip is 25 µl/min. Other flow rates are defined by the desired mixing ratios of the reagents involved relative to 25 µl/min.

In the microfluidic device shown in FIG. 7 lysis and quench reagents are added from both sides of the reaction channel. This is to aid mixing of the blood and the added reagent. It may be desirable to introduce reagent from only one side or to have multiple introductions of the same reagent along the length of the reaction channel. Where this is necessary a similar design approach to the one described would be applicable.

Microfluidic devices made using the design rationale described could be manufactured in any of the materials commonly used for micro fabricated devices.

Figure 8:
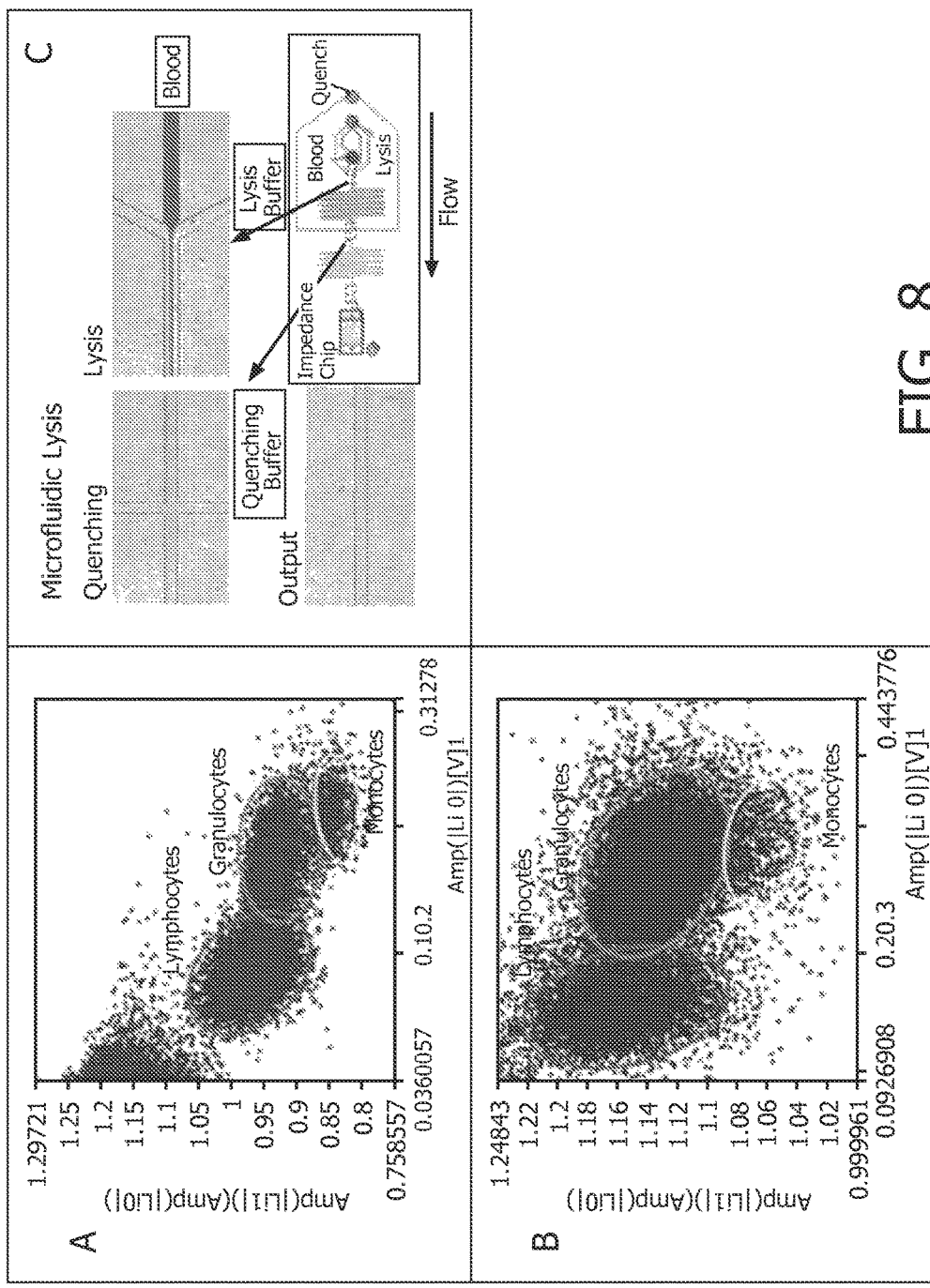
FIG. 8A shows 3 part impedance spectroscopy using standard bench 'bulk' preparation techniques.
FIG. 8B shows impedance spectroscopy of the blood after microfluidic lysis and quench.
FIG. 8C shows micrographs of the microfluidic lysis and quench steps in process.

In FIG. 8A, 3 Part Impedance spectroscopy using standard bench 'bulk' preparation techniques is shown. FIG. 8B shows impedance spectroscopy of the blood after microfluidic lysis and quench. FIG. 8C shows micrographs of the microfluidic lysis and quench steps of the microfluidic device in operation. Impedance spectroscopy of the blood, post lysis reveals populations of cells in good agreement with those obtained when the lysis was performed using standard laboratory procedures (Compare FIGS. 8B and 8A) and in proportions consistent with those expected in human blood. These results confirm that microfluidic lysis can be achieved within a micro fluidic system using a system of balanced fluidic resistances and under the control of only a single syringe pump.

The microfluidic device according to the invention enables large dilutions to be performed. In standard laboratory procedure large dilutions are performed in a serial fashion where dilution is achieved by performing several smaller dilutions (such that for a 1:10,000 dilution four sequential 1:10 dilutions of the sample might be performed). Such a procedure requires a skilled individual to perform the many pipetting steps, often using large amounts of reagent and time. In moving such a dilution protocol to a micro fluidic format, for example for use in a medical device to be used by an unskilled individual, it is desirable to reduce the amount of reagent used (lowering the cost of the overall device) and to minimise the time needed to run the device (fast start-up). In addition, as with the lysis device described above, it would be preferable in terms of cost if such a device used as few hydrodynamic pumps as possible. Such a device would have application in a point of care haematology analyser where the quantity of red blood cells within the blood makes large dilution necessary.

As with the standard laboratory technique, dilution on the micro fluidic platform is by a sequence of smaller dilutions (this can be by any combination, such that a 1:10,000 dilution can be achieved by four 1:10 dilutions, two 1:100 dilutions or any other combination that achieves a 1; 10,000 dilution). Fast start up and minimal reagent usage are achieved by discarding the majority of the sample prior to each dilution step (such that at each dilution step only a small amount of the already dilute sample gets further diluted). As with the lysis device the two reagents (blood and diluent) are stored under atmospheric pressure in a reservoir on the fluidic block. Detection of the diluted blood is by flow through impedance spectroscopy (the detection chip is again integrated on the microfluidic block).

Figure 9:
FIG. 9 shows an embodiment of a microfluidic diluter 100.

In this case flow rates through the microfluidic block are dictated by the desired rate for detection at the impedance chip 33 and by the required dilution ratios. FIG. 9 shows an example of a microfluidic diluter 100. Thus for a 1:10,000 dilution by four sequential 1:10 dilutions with a desired flow rate of 40µl/min at the detection chip 33 the flow rates through the fluidic block are as shown in FIG. 9. In this example the blood enters the device at 4 µl/min and is diluted 1:10. In the device shown in FIG. 9, following each dilution step there is a channel with residence time of 30 seconds to facilitate mixing of the blood with diluent (this could be substituted by active mixing structures built into the device which might reduce the time needed in these sections). Before undergoing further dilution steps 9/10ths of the, now diluted, blood is channelled to waste with 1/10th continuing along the device where it undergoes a further 1:10 dilution. This process is repeated along the fluidic block until the blood is diluted 10,000 times where it is channelled through the impedance chip 33 and detected. The waste is combined at each stage and is channelled straight to the waste syringe (bypassing the chip 33).

Within the diluter device relative flow rates of the fluidic channels are again controlled by modification of the fluidic resistances by adjusting the length, width and height of the fluidic channels according to the equation described above. The more complicated network of fluidic resistances found in this structure necessitates use of a number of possible design tools, for instance a circuit simulator.

Figure 10:
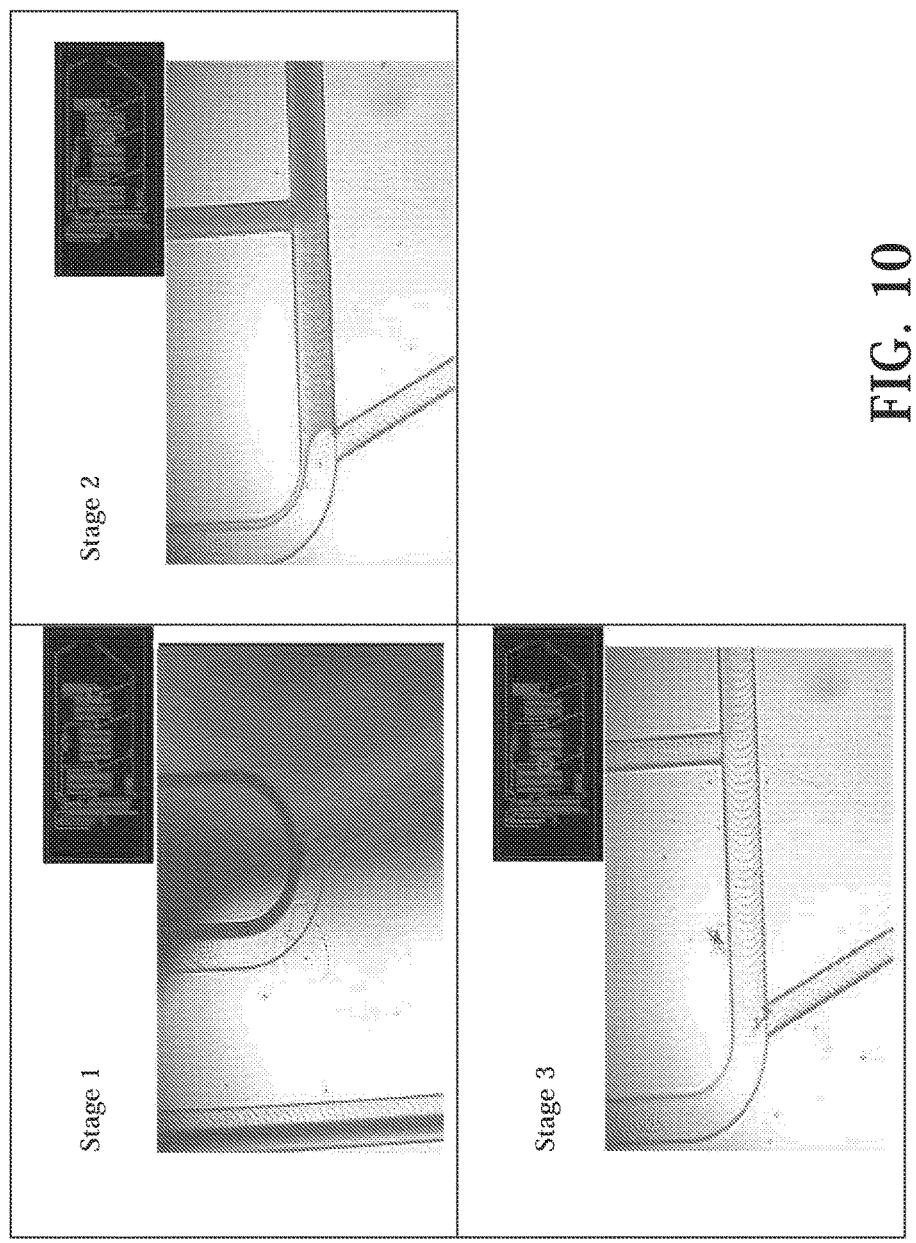
FIG. 10 Microscope images of the working diluter

FIG. 10 shows microscope images of the diluter working. The Stages 1-3 correspond to different positions in FIG. 9.

The individual elements described above (microfluidic red blood cell lysis, haemoglobin detection and 1:10,000 dilution) can be combined using the same design rationale described for the above devices.

Figure 11:
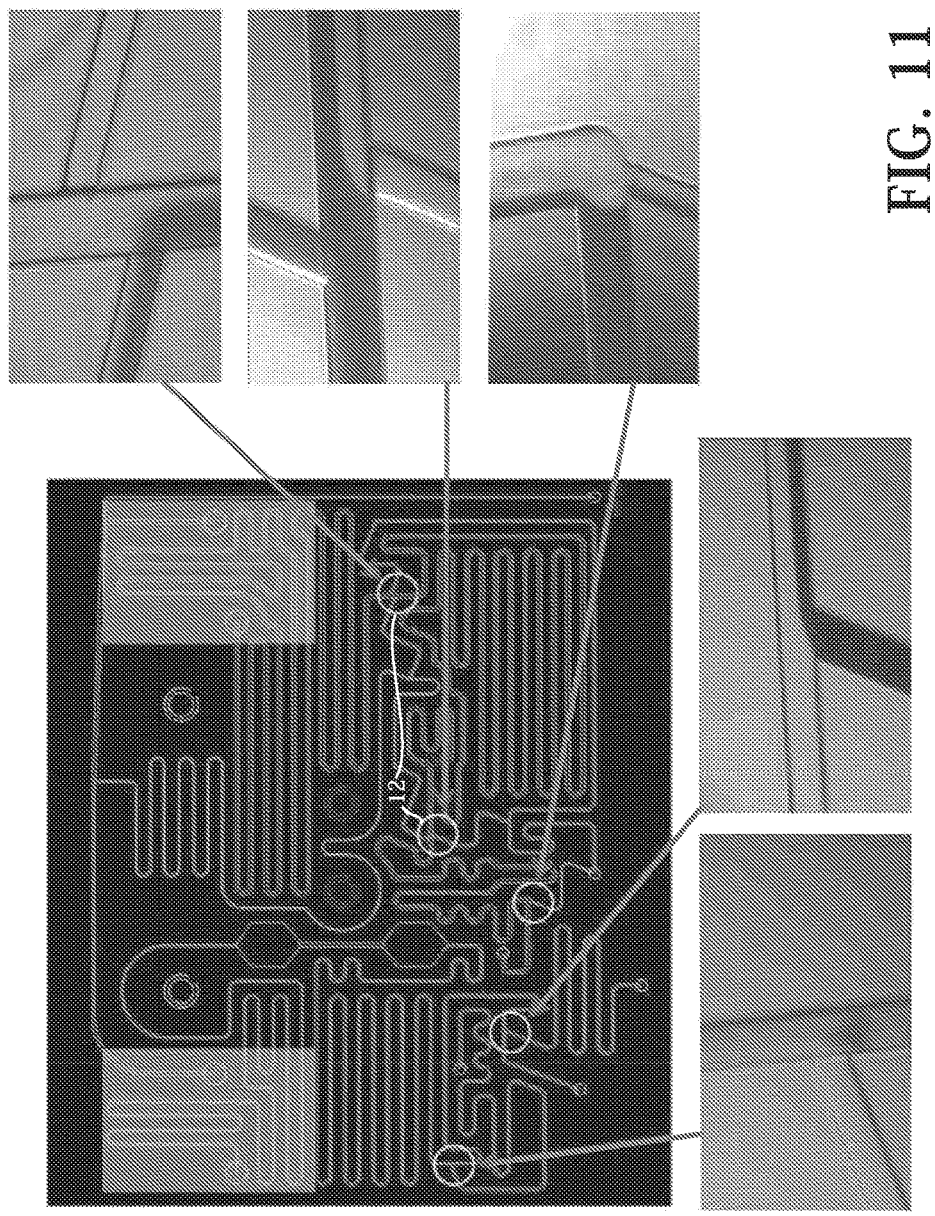
FIG. 11 illustrates an embodiment of the integrated microfluidic lysis, dilution and haemoglobin measurement device.

FIG. 11 shows the microfluidic block and blood/reagent flow in micrographs of the relevant parts operating.

Figure 12:
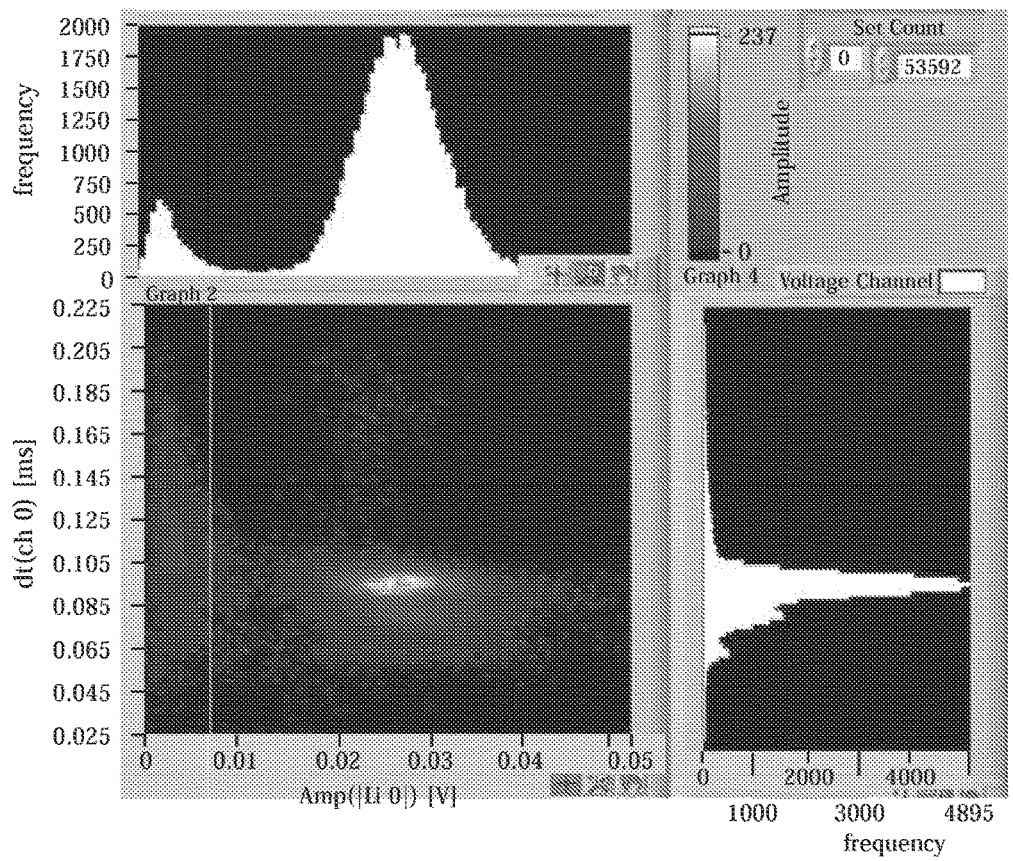
FIG. 12 shows experimental cell counts obtained with the microfluidic device.

FIG. 12 shows experimental cell counts obtained with this system.

It is to be understood that although preferred embodiments, specific constructions and configurations, as well as materials, have been discussed herein for devices according to the present invention, various changes or modifications in form and detail may be made without departing from the scope of this invention as defined by the appended claims.

The invention claimed is:

1. A microfluidic device for performing a full blood count from a whole blood sample from a finger-prick, the full blood count including measurements of white blood cell differential count, platelet count, red blood cell counts and hemoglobin, the microfluidic device comprising:
    a first inlet for providing the whole blood sample;
    a second inlet for providing a first lysis agent to count white blood cells, the second inlet being located downstream from the first inlet and being connected to a first junction;
    a third inlet for providing a quench solution, the third inlet being located downstream from the second inlet and being connected to a second junction;
    a first pair of channels connected to and split from the first inlet and meeting at the first junction,
    a second pair of channels connected to and split from the third inlet and meeting at the second junction;
    a first snake mixing stage configured to mix the first lysis agent and the whole blood sample, the first snake mixing stage being located between the second and third inlets;
    a second snake mixing stage configured to mix the quench solution and the mixture of the first lysis agent and the whole blood sample mixed at the first snake mixing stage, the second snake mixing stage being serially connected to the first snake mixing stage and located downstream from the first snake mixing stage and the third inlet, wherein an input of the first snake mixing stage is connected to the first junction, to the second inlet and to the first pair of channels, and wherein an output of the first snake mixing stage is connected to the second junction, to an input of the second snake mixing stage, and to the second pair of channels for providing the quench solution to the input of the second snake mixing stage from the second pair of channels split from the third inlet and meeting at the second junction; and
    a channel for providing a second lysis agent to measure the hemoglobin, the channel including a fourth inlet located downstream from the first inlet for providing the second lysis agent into the channel to measure the hemoglobin.

2. The microfluidic device according to claim 1, further comprising a first sensor that determines the white blood cell differential count at an end of the first channel.

3. The microfluidic device according to claim 2, wherein the first sensor measures impedance.

4. The microfluidic device according to claim 3, further comprising a second sensor that determines properties of red blood cells at an end of the second channel.

5. The microfluidic device according to claim 4, wherein the second sensor is optical.

6. The microfluidic device according to claim 5, further comprising a microfluidic chamber in between the second channel and the second sensor.

7. The microfluidic device according to claim 1, further comprising a microfluidic diluter.

8. The microfluidic device according to claim 1, further comprising a single hydrodynamic pump.

9. The microfluidic device of claim 1, wherein the second inlet is connected to an end of the first snake mixing stage near the first inlet and is for providing the first lysis agent to the first snake mixing stage of first channel to count the white blood cells, and wherein the third inlet is connected to an end of the second snake mixing stage between the first snake mixing stage and the second snake mixing stage.

10. The microfluidic device of claim 1, wherein the volume is between 10 µl to 50 µl.

11. The microfluidic device of claim 1, wherein a flow rate of the whole blood sample at the first inlet is about 3 µl/min, a flow rate of the first lysis agent at the second inlet is about 37 µl/min and a flow rate of the quench solution at the third inlet is about 16.3 µl/min.

12. The microfluidic device of claim 11, wherein the first lysis agent and the whole blood sample are mixed by diffusion over a length of the first snake mixing stage, the length enables a time of contact between the first lysis agent and the blood sample to be between 5 and 7 seconds.

13. The microfluidic device of claim 1, wherein at least one of the first quench channel and the second quench channel meeting at the junction forms an acute angle with a portion of the first channel downstream of the junction.

* * * * *